|   | United States Patent [19] | [11] | 4,043,791 |
|---|---|---|---|

Krumkalns [45] Aug. 23, 1977

[54] METHOD OF REGULATING THE GROWTH OF AQUATIC WEEDS WITH PYRIDINE DERIVATIVES

[75] Inventor: Eriks V. Krumkalns, Indianapolis, Ind.

[73] Assignee: Eli Lilly and Company, Indianapolis, Ind.

[21] Appl. No.: 673,040

[22] Filed: Apr. 2, 1976

[51] Int. Cl.$^2$ ............................................. A01N 9/22
[52] U.S. Cl. .......................................... 71/66; 71/94; 260/290 R; 260/290 HL
[58] Field of Search ....................................... 71/94, 66

[56] References Cited

U.S. PATENT DOCUMENTS

| 3,244,722 | 4/1966 | Johnston et al. ........................ 71/66 |
| 3,655,359 | 4/1972 | Krumkalns et al. ...................... 71/94 |
| 3,746,531 | 7/1973 | Doherty .................................. 71/66 |

*Primary Examiner*—Lewis Gotts
*Assistant Examiner*—Catherine L. Mills
*Attorney, Agent, or Firm*—Dwight E. Morrison; Everet F. Smith

[57] ABSTRACT

A method of regulating the growth of submerged and floating aquatic weeds which comprises adding a fluoroalkoxyphenyl-substituted 3-pyridinemethanol to a body of water containing the submerged and floating aquatic weeds to be regulated, in quantities sufficient to regulate the growth of the said submerged and floating aquatic weeds. The disclosure also relates to novel compositions for carrying out the method.

4 Claims, No Drawings

METHOD OF REGULATING THE GROWTH OF AQUATIC WEEDS WITH PYRIDINE DERIVATIVES

BACKGROUND OF THE INVENTION

1. Field of the Invention

The field of the invention relates to the regulation of the growth of aquatic weeds in canals, rivers, ponds, lakes, and impoundments.

2. Description of the Prior Art

The problems of controlling or regulating the growth of organisms in aqueous systems are serious and growing in severity. Submerged aquatic weeds, for example, cause major problems in water distribution and irrigation systems. The growth of such weeds in irrigation canals greatly reduces the conductivity and capacity of such systems with resulting substantial economic loss. Large sums are spent in the mechanical and other methods of removal of weed growths from irrigation canals, especially in the western parts of the United States. Because of the great difficulties involved in the mechanical removal of weeds and other undesired forms of aquatic life from irrigation canals, ponds, lakes, impoundments, etc., it has been proposed to utilize chemical control. Accordingly, various types of chemicals have been added to such bodies of water.

However, with the growing emphasis on conservation, current efforts are directed toward regulating the growth, that is, limiting or inhibiting the amount of growth accomplished by the naturally occurring submerged or floating aquatic weeds without killing those weeds. This approach is being taken in order to continue to provide the natural environment for fish and other forms of marine life. A further reason is to avoid the masses of dead and rotting aquatic weeds which result when said weeds are killed by means of an aquatic herbicide, since the decomposition of the weeds decreases the amount of available oxygen present in the water. Such decaying matter, when it occurs in reservoirs and/or streams from which drinking water for cities is obtained, makes purification of the water more difficult. Such decaying vegetation also gives off an unpleasant odor when it collects in a body of water. Thus, a control of the amount of growth, rather than a destruction of the submerged aquatic weeds, serves to overcome both pollution of the water and pollution of the air.

In the prior art, Krumkalns et al., U.S. Pat. No. 3,655,359 (Apr. 11, 1972), teach the use of substituted 3-pyridylmethanes for eliminating germinating weed grasses and broadleaf weeds selectively from crop plants such as corn, cotton, and soybeans, and their close relatives in the plant kingdom, and also for inhibiting the growth of suckers on tobacco plants. None of the compounds in the reference have fluoroalkoxy substituents, and there is no teaching that if the compounds disclosed therein were modified to give the compounds disclosed in the instant application, such compounds would thereby possess aquatic growth regulating properties.

Also in the prior art, Krumkalns et al., U.S. Pat. No. 3,744,988 (July 10, 1973), teach the use of substituted 3-pyridylmethanes in a method for inhibiting sucker growth to tobacco plants. This patent is a division of U.S. Pat. No. 3,655,359, supra, and includes in its disclosure many of the same compounds disclosed therein. There are no fluoroalkoxy-substituted 3-pyridine compounds disclosed in this reference, either, nor teaching that would make their utility as aquatic growth regulators obvious.

Van Heyningen, U.S. Pat. No. 3,396,224 (Aug. 6, 1968), teaches a method of controlling fungi pathogenic to plants by contacting the fungus-susceptible plant with a fungicidal amount of a 3pyridylmethane derivative, mainly a 3-pyridinemethanol. No fluoroalkoxy-substituted 3-pyridine compounds are taught in this reference, nor are there any suggestions that such substituted pyridine compounds would be useful as aquatic growth regulators.

Van Heyningen et al., U.S. Pat. No. 3,397,273 (Aug. 13, 1968), teaches and claims a method for protecting plants from attack by phytopathogenic fungi by treating the plants with a fungicidally-effective amount of a 3-pyridylmethane. No fluoroalkoxy-substituted 3-pyridine compounds are taught in this reference, and there are no suggestions that such compounds would be useful as aquatic growth regulators.

Another prior art reference is Belgian Pat. No. 816,245 (Nov. 20, 1974), which teaches the preparation, inter alia, of the fluoroalkoxy-substituted 3-pyridinemethanol compounds found useful in the present invention. This Belgian reference teaches the utility of the disclosed compounds as herbicides, plant fungicides and as terrestrial plant growth regulators, with activity being shown in tests on soybean, chrysanthemum, and turf. There is no teaching or suggestion that the compounds would have utility as aquatic plant growth regulators.

Another reference is German Pat. No. 1,935,292, also identified by Derwent No. 04548S, which patent teaches and claims a means for controlling plant growth, that is, restraining growth and influencing the habits of higher plants, influencing blossom and fruit formation, checking the growth of grass, and the like, using tri-arylmethylimidazoles, -pyrazoles, and -triazoles, or their salts. One of the aryl groups is taught as pyridyl. The reference does not appear to include use on aquatic weeds or plants.

Yet another reference is British Pat. No. 1,274,578, also identified by Derwent No. 23143S. This reference teaches plant growth regulators containing N-benzylimidazoles, wherein one of the substituents is a pyridyl group. These compounds are alleged to be plant growth regulators capable of inhibiting or accelerating growth, flowering and fruiting, according to the amount applied. Certain of the compounds are also alleged to be plant fungicides and bactericides. Neither of these last two references have any fluoroalkoxy substituents mentioned in them for attachment to the pyridine nuclei therein.

SUMMARY OF THE INVENTION

The present invention relates to a method of regulating the growth of submerged and floating aquatic weeds by adding to the water containing such submerged and floating aquatic weeds a growth-regulating and non-herbicidal amount of a fluoroalkoxyphenyl-substituted 3-pyridinemethanol.

DESCRIPTION OF THE PREFERRED EMBODIMENT

This invention relates to a novel method for regulating the growth of submerged and floating aquatic weeds. More particularly, this invention relates to a novel method and compositions for regulating the growth of submerged and floating aquatic weeds which comprises adding to the water containing said weeds a growth-regulating and non-herbicidal amount of a compound of the formula

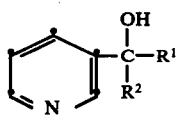

I wherein
R¹ is $C_1$–$C_6$ alkyl, phenyl, or $C_3$–$C_8$ cycloalkyl;
R² is trifluoromethoxyphenyl, 1,1,2,2,-tetrafluoroethoxyphenyl, pentafluoroethoxyphenyl, or 3,4-(difluoromethylenedioxy) and
the nonphytotoxic acid addition salts thereof.

In the above formula, $C_1$–$C_6$ alkyl is a branched or straight-chain saturated alkyl, and can be methyl, ethyl, n-propyl, isopropyl, n-butyl, sec.-butyl, isobutyl, n-amyl, isoamyl, sec.-amyl, n-hexyl, sec.-hexyl, or isohexyl.

$C_3$–$C_8$ Cycloalkyl represents a monocyclic saturated cycloalkyl such as cyclopropyl, cyclobutyl, cyclopentyl, cyclohexyl, cycloheptyl, or cyclooctyl.

The fluoroalkoxy-substituted 3-pyridinemethanol compounds useful in the novel method of this invention are prepared utilizing a halo-substituted pyridine as the key starting material, preferably 3bromopyridine. This bromopyridine compound is known to those skilled in the art, and its preparation has been described in the literature. This particular compound is preferred because of its ready availability and its excellent reaction in the condensation reactions.

The preparation of these fluoroalkoxy-substituted 3-pyridine compounds is carried out in the following manner. A solvent composed of equal volumes of tetrahydrofuran and ethyl ether is cooled to a temperature of about −30° to −40° C., under an atmosphere of dry nitrogen, with moisture excluded. A n-hexane solution of n-butyllithium is added thereto, and the whole cooled to a temperature of about −70° C. The 3-bromopyridine is dissolved in a suitable solvent, preferably anhydrous ethyl ether, and this ether solution is added dropwise to the tetrahydrofuran-ether solution of the n-butyllithium, while maintaining the temperature at about −70° C. A suitable ketone, for example, isopropyl p-trifluoromethoxyphenyl ketone, dissolved in anhydrous tetrahydrofuran-ethyl ether mixture (1:1), is then added to the reaction mixture. The reaction mixture is stirred overnight in the cold (−60° to −70° C.) The reaction product mixture is then worked up by adding dilute aqueous ammonium chloride solution. The organic layer is separated and dried over a suitable drying agent. The dried organic layer is concentrated to dryness in vacuo and the residue is chromatographed on a silica column using acetone-benzene diluent. The desired product is eluted from the column using a suitable eluent, for example, one composed of 10 percent acetone and 90 percent benzene by volume. The eluate, which contains the product, is concentrated in vacuo. The product, a heavy oil, is identified by elemental analyses, NMR, and IR spectra, as α-isopropyl-α-[p-(trifluoromethoxy)phenyl]-3-pyridinemethanol.

Other fluoroalkoxyphenyl-substituted 3-pyridinemethanols which can be prepared by the same general method, and which are usable in the instant novel aquatic growth regulator method, include the following:

α-Methyl-α-[p-(trifluoromethoxy)phenyl]-3-pyridinemethanol
α-Ethyl-α-[p-(trifluoromethoxy)phenyl]-3-pyridinemethanol
α-(n-Propyl)-α-[p-(trifluoromethoxy)phenyl]-3-pyridinemethanol
α-Phenyl-α-[p-(1,1,2,2-tetrafluoroethoxy)phenyl]-3-pyridinemethanol
α-Ethyl-α-[p-(pentafluoroethoxy)phenyl]-3-pyridinemethanol
α-Methyl-α-[3,4-(difluoromethylenedioxy)phenyl]-3-pyridinemethanol
α-Cyclopropyl-α-[p-(trifluoromethoxy)phenyl]-3-pyridinemethanol.HCl
α-Cyclobutyl-α-[p-(1,1,2,2-tetrafluoroethoxy)-phenyl]-3-pyridinemethanol.HBr
α-Cyclopentyl-α-[p-(pentafluoroethoxy)phenyl]-3-pyridinemethanol
α-cyclohexyl-α-[p-(trifluoromethoxy)phenyl]-3-pyridinemethanol, and the like.

The nonphytotoxic acid addition salts of the above-prepared compounds are readily prepared by methods well known to the art. Thus, the free base is dissolved in ether, the solution cooled and saturated with, for example, anhydrous hydrogen chloride gas. The hydrochloric acid addition salt of the substituted compound precipitates and is filtered off and purified by recrystallization.

The ketone intermediates used in the preparation of the above-described compounds of this invention are compounds of the formula

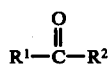

II wherein R¹ and R² are identified in the same manner as set forth hereinabove for formula I.

The preparations of these ketones are accomplished according to a number of procedures appearing in the prior art. The intermediate p-trifluoromethoxybromobenzene is commercially available. The ketones bearing the p-trifluoromethoxyphenyl substituent are then prepared by standard methods from the p-trifluoromethoxybromobenzene intermediate. Thus, the Grignard reagent prepared from p-trifluoromethoxybromobenzene is allowed to react with an alkyl nitrile, for example, isobutyronitrile to yield an alkyl p-trifluoromethoxyphenyl ketone, in the present case, isopropyl p-trifluoromethoxyphenyl ketone.

The preparation of ketones containing the 3,4-(difluoromethylenedioxy)phenyl moiety is accomplished by first synthesizing 3,4-(difluoromethylenedioxy)-bromobenzene according to the procedure of Stogryn, Jour. Org. Chem. 37, 673, (1972). This substituted bromobenzene is then allowed to react with an aldehyde, for example, isobutyraldehyde, in the presence of n-butyllithium, at about −40° C., to yield the intermediate alcohol, isopropyl 3,4-(difluoromethylenedioxy)phenyl carbinol. This alcohol is oxidized using chromium trioxide in aqueous acetic acid to yield isopropyl 3,4-(difluoromethylenedioxy)phenyl ketone. Additional 3,4-(difluoromethylenedioxy)phenyl substituted ketones, alkyl or aryl, can be prepared in the same general manner.

The preparation of pentafluoroethoxy-substituted phenyl alkyl ketones is accomplished following the procedure of Belous et al., *J. Org. Chem.* (U.S.S.R.) 7, 1521 (1971). According to that procedure, p-bromophenol is allowed to react with trifluoroacetic anhydride in the presence of sulfur tetrafluoride and hydrogen fluoride, to yield pentafluoroethoxy-4-bromobenzene. This compound is allowed to react with isobutyraldehyde in the presence of n-butyllithium to yield the intermediate alcohol, isopropyl p-(pentafluoroethoxy)-phenyl carbinol. This alcohol is oxidizied with chromium trioxide in the presence of aqueous acetic acid to yield the ketone, isopropyl p-(pentafluoroethoxy)phenyl ketone.

The compound, 1,1,2,2-tetrafluoroethoxy-4-bromobenzene, is commercially available. It is used to prepare a Grignard reagent, which is in turn allowed to react with isobutyronitrile to yield one of the desired ketones, isopropyl p-(1,1,2,2-tetrafluoroethoxy)phenyl ketone. Other p-(1,1,2,2-tetrafluoroethoxy)phenyl substituted alkyl or aryl ketones are prepared in the same general manner.

The syntheses of these intermediate ketones are set forth hereinbelow.

PREPARATION 1

Isopropyl p-trifluoromethoxyphenyl ketone

Using about 800 ml. of anhydrous tetrahydrofuran as solvent, the Grignard reagent was prepared from 50 g. of p-bromophenyltrifluoromethyl ether and 5.5 g. of magnesium turnings. To the Grignard reagent thus prepared, 15 g. of isobutyronitrile was added slowly, dropwise. The addition of the nitrile required about ½ hour. The reaction mixture was heated to refluxing for about 10 hours, cooled, and decomposed by the addition of aqueous 1N hydrochloric acid with stirring, to a ph of approximately 3. The aqueous layer was separated from the organic layer and the aqueous layer was discarded. The organic layer was dried over anhydrous magnesium sulfate. The drying agent was then filtered off and the filtrate was concentrated in vacuo. The residue was distilled to yield a liquid product having a boiling point of about 97°–98° C., at house vacuum pressure. The product weighed 19 g. It was identified by infrared spectrum as isopropyl p-trifluoromethoxyphenyl ketone.

PREPARATION 2

Isopropyl p-pentafluoroethoxyphenyl ketone

Starting with 4-bromophenol, the preparation of 4-bromopentafluoroethoxybenzene was carried out following the procedure of Belous et al., *J. Org. Chem.* (U.S.S.R.) 7, 1521 (1971).

To a solution of 15 g. of the thus prepared 4-bromopentafluoroethoxybenzene in 200 ml. of anhydrous ethyl ether, was added 25 ml. of a 22 percent solution of n-butyllithium in n-hexane. The mixture was cooled to about −60° C., and while being maintained at this temperature, there was added slowly to the mixture a solution of 10 g. of isobutyraldehyde in 200 ml. of anhydrous ethyl ether. The reaction mixture was maintained at about −60° C., and stirred overnight, followed by stirring for a period of about 48 hours at room temperature.

The reaction product mixture was worked up by the addition of aqueous ammonium chloride solution. The organic phase was separated and dried over anhydrous magnesium sulfate. The drying agent was filtered off.

The filtrate was concentrated in vacuo to yield product having a weight of about 23 g. The product was identified by infrared spectrum as isopropyl p-pentafluoroethoxyphenyl carbinol.

The carbinol thus prepared, 20 g., was dispersed in 200 ml. of glacial acetic acid with stirring, and to the mixture was added 20 g. of chromium trioxide dissolved in 30 ml. of water. The addition was carried out carefully and the reaction temperature was kept below 80° C. Stirring of the mixture was continued for about 4 hours. The reaction product mixture was cooled and poured onto a mixture of crushed ice and aqueous 50 percent sodium hydroxide solution, and the ph adjusted to pH 8. The mixture was extracted with large volumes of ether, and the ether extracts combined and washed with dilute aqueous sodium hydroxide solution. The ether solution was dried and concentrated in vacuo. The residue was chromatographed over a silica column using benzene as solvent and eluent, to yield 7 g. of product, which was identified by NMR and infrared spectra as isopropyl p-pentafluoroethoxyphenyl ketone.

PREPARATION 3

3,4-(Difluoromethylenedioxy)phenyl isopropyl ketone

A mixture of 50 g of 3,4-(methylenedioxy)bromobenzene and 200 g. of phosphorus pentachloride was heated at about 80° C. for about 4 hours. At the end of this time, the reaction product mixture was distilled and the material boiling at 115°–125° C. was collected. It weighed about 42 g. and was identified by NMR spectrum as 3,4-(dichloromethylenedioxy)bromobenzene.

A mixture of 3,4-(dichloromethylenedioxy)bromobenzene, 42 g., and 28 g. of antimony trifluoride was heated under reduced pressure. At approximately 80°–82° C., the product distilled over, and there was collected 34 g, of product, which was identified by elemental analyses as 3,4-(difluoromethylenedioxy)-bromobenzene.

To 56 g. of 3,4-(difluoromethylenedioxy)bromobenzene in 250 ml. of tetrahydrofuran was added 110 ml. of a 22 percent solution of n-butyllithium in n-hexane at about −70° C., in an atmosphere of nitrogen. To this mixture was added 16 g. of isobutyraldehyde, and the reaction mixture was stirred overnight at about −70° C. The reaction product mixture was worked up by pouring it into a concentrated aqueous ammonium chloride solution with stirring. The organic layer was separated and dried. The drying agent was filtered off and the organic solvent removed in vacuo. A total of about 27 g. of the crude carbinol, 3,4-(difluoromethylenedioxy)-phenyl isopropyl carbinol, was obtained and used without further purification in the next step.

Following the same general procedure as described in Preparation 2, the carbinol, 27 g., was oxidized with chromium trioxide in glacial acetic acid, to yield 3,4-(difluoromethylenedioxy)phenyl isopropyl ketone, weighing about 16 g., and identified by NMR spectrum.

PREPARATION 4

Cyclohexyl 3,4-(difluoromethylenedioxy)phenyl ketone

To a solution of 24 g. of 3,4-(difluoromethylenedioxy)bromobenzene in 250 ml. of ether was added 2.4 g. of magnesium shavings. To the Grignard reagent thus prepared was added 11 g. of cyclohexylcarboxaldehyde in 50 ml. of anhydrous ethyl ether. The reaction mixture was allowed to stir for about 2–3 hours. The reaction product mixture was worked up by adding to it at room temperature a concentrated aqueous solution of ammonium chloride. The organic layer was separated, dried, filtered from the drying agent, and concentrated in vacuo. The residue, which is the crude carbinol, was oxidized with chromium trioxide and glacial acetic acid. The oxidation was worked up by pouring onto a mixture of crushed ice and 50 percent aqueous sodium hydroxide. The mixture was extracted with ethyl ether. The ether solution was dried, the drying agent filtered off, and the filtrate concentrated in vacuo. The residue thus obtained was dissolved in benzene and chromatographed over a silica column using benzene as the eluent. There was obtained about 8 g. of cyclohexyl 3,4-(difluoromethylenedioxy)phenyl ketone, identified by its infrared and NMR spectra.

The following examples describe in detail the methods used in preparing the compounds for use in the novel method of this invention.

EXAMPLE 1

α-Isopropyl-α-[p-trifluoromethoxy)phenyl]-3-pyridinemethanol

To a solution of 250 ml. of a mixture of equal volumes of tetrahydrofuran and ethyl ether, cooled to about −30° to about −40° C., and maintained under an atmosphere of dry nitrogene gas, was added 50 ml. of a 15 percent solution of n-butyllithium in n-hexane. The mixture was stirred and cooled to about −70° C, and there was added thereto a solution of 16 g. of 3-bromopyridine in 250 ml. of the 50:50 by volume mixture of tetrahydrofuran and ethyl ether. After the addition was complete, the reaction mixture was allowed to stir for about ½ hour. A solution of 20 g. of isopropyl p-trifluoromethoxyphenyl ketone in 100 ml. of the mixture of tetrahydrofuran and ethyl ether was then added dropwise with stirring. The resulting reaction mixture was maintained at about −70° C., while being stirred overnight.

The reaction product mixture was allowed to warm to room temperature, and aqueous ammonium chloride solution was added. The aqueous and organic layers were separated. The organic layer was washed with water and dried over anhydrous magnesium sulfate. The drying agent was filtered off and the filtrate was concentrated to yield a yellow oil having a weight of about 43 g. This oil was chromatographed on a silica column, and the desired product was eluted from the column using a solvent mixture of 10 percent acetone and 90 percent benzene by volume. The acetone-benzene eluate was concentrated in vacuo, to yield a yellow oil weighing about 11 g. On standing, the oil solidified. The solid was recrystallized from hot ether to yield white crystals having a melting point of about 81°–82° C. The crystalline product was identified by NMR spectrum as α-isopropyl-α-[p-trifluoromethoxy)phenyl]-3-pyridinemethanol.

Following the same general procedure set forth hereinabove and using suitable starting materials, the following compound was synthesized:

1A. α-Cyclohexyl-α-[p-1,1,2,2-tetrafluoroethoxy)phenyl]-3-pyridinemethanol. Melting point: oil. Structure identified by NMR spectrum.

The novel method of this invention is practiced by adding the active substituted pyridine compounds to the water containing the submerged and or floating aquatic weeds. The compounds may be applied to the water as dusts when admixed with a powdered solid carrier such as various mineral silicates, e.g., mica, talc, pyrophyllite, and clays. The compounds may be mixed with surface-active dispersing agents to form concentrates to facilitate dispersion in water and and to improve the wetting properties when used as sprays. If desired, the compounds may be mixed with a powdered solid carrier, together with a surface-active dispersing agent, so that a wettable powder may be obtained which may be applied directly, or which may be shaken up with water to make an aqueous dispersion for application in that form. The compounds may be dissolved in an oil such as a hydrocarbon or chlorinated hydrocarbon oil, and the oil solution of the compound dispersed in water with the aid of a surface-active dispersing agent to give a sprayable aqueous dispersion. Such surface-active dispersing agents may be anionic, nonionic, or cationic surface-active agents. Such surface-active agents are well known, and reference is made to Hoffmann et al., U.S. Pat. No. 2,614,916, columns 2–4, for detailed examples of the same. The compounds useful in the present invention may also be applied by the aerosol method. Solutions for the aerosol treatment may be prepared by dissolving the compound directly in the aerosol carrier, which is a liquid under pressure, but which is a gas at ordinary temperature (e.g. 20° C.) and atmospheric pressure; or, the aerosol solution may be prepared by first dissolving the compound in a less volatile solvent, and then admixing such solution with the highly volatile liquid aerosol carrier.

The invention is practiced by adding to the water containing the submerged and floating weeds a growth-regulating and non-herbicidal amount of a compound, such that a concentration of from about 0.25 to about 10 ppm. of the active compound is attained.

The optimum concentration of compound for any specific control problem varies with the temperature, the species to be controlled, and the shape of the water body to be treated. At higher water temperatures, less compound is generally required for a given degree of control than is needed at lower temperatures.

In considering the treatment of moving streams for the purpose of controlling flora fixed therein, special account must be taken of the fact that the compounds will pass over the area to be treated and that the concentration during the contact period is dependent upon the water flow rate, the rate of chemical addition, and the period of addition.

The novel aquatic growth regulating method and compositions for use therein are illustrated by the following experiments.

EXPERIMENT 1

The following method was used in the laboratory to evaluate the aquatic growth regulating property of a selected compound of those disclosed herein when used at a concentration of 10 ppm. against a representative submerged aquatic weed.

The compound for this test, α-isopropyl-α-[p-(trifluoromethoxy)phenyl]-3-pyridinemethanol, was formulated in the following manner. Twenty mg. of the compound was weighed into a 12 ml. disposable vial. To the vial containing the compound were added 1 ml. of acetone and 9 ml. of aqueous 0.1 percent polyoxyethylene sorbitan monooleate (Tween 80). To obtain the test concentration of 10 ppm., 4.00 ml. of this stock solution was added to 785 ml. of water in a plastic container. The plastic containers used were flowerpotshaped, having a bottom diameter of 9 cm., a top diameter of 11.5 cm. and a height of 13.5 cm.

Terminal pieces of Florida elodea (*Hydrilla verticillata* (L.F.)), hereinafter identified as hydrilla, 10 cm. long, without branching, were prepared for testing. Three such cuttings were placed in each plastic container holding 785 ml. of water, to which water the formulated test compound had been added, along with 3 ml. of Hoagland's Nutrient solution. Three 10 cm. cuttings of hydrilla were placed in each of several control containers of water, along with the amount of solvent used to formulate the test compound also in each container.

After a period of 2 to 3 weeks, measurements were made to determine the total length of each plant. An average total growth was obtained by dividing the total combined lengths by the number of replicates. By subtracting 10 cm. from the average total length, the average increase in growth was obtained. This difference was divided by the average increase in length of the plants in the solvent controls (SC), and the quotient multiplied by 100 to give a percent inhibition. The calculations were carried out using the following formula:

$$\frac{\text{Total combined length of Replicates}}{\text{Number of Replicates}} = \text{Average Length}$$

Avg. Length − 10 cm. = Avg. Increased Growth $$\left(1 - \frac{\text{Avg. Increased Growth}}{\text{Avg. Increased Growth SC}}\right) \times 100 = \% \text{ Inhibition}$$

The compound employed in the Experiment, α-isopropyl-α-[p-(trifluoromethoxy)phenyl]-3-pyridinemethanol, produced a growth inhibition of the *Hydrilla verticillata* of approximately 97 percent.

A further test of this compound was conducted according to the following described procedure.

EXPERIMENT 2

The general procedure of Experiment 1 was repeated using the same compound at test concentrations of 1, 0.5 and 0.25 ppm.

The test compound was formulated in the following manner: Twenty mg. of compound was weighed into a 12 ml. disposable vial. To the vial containing the compound were added 1 ml. of acetone and 9 ml. aqueous 0.1 percent polyoxyethylene sorbitan monooleate. This solution was designated as stock solution A.

The 1 ppm. test concentration was obtained as follows: Four ml. of stock solution A was diluted with 36 ml. of aqueous 0.1 percent polyoxyethylene sorbitan monooleate to give stock solution B. Four ml. of stock solution B, when added to 785 ml. water in the plastic test containers, gave a concentration of test compound of 1 ppm. The plastic containers were identified to those employed in Experiment 1.

The 0.5 ppm. concentration of test compound was obtained as follows: Stock solution B, 20 ml., was diluted with 20 ml. aqueous 0.1 percent polyoxyethylene sorbitan monooleate, and this solution was designated stock solution C. Four ml. of stock solution C was added to 785 ml. of water in the plastic test containers to give a concentration of 0.5 ppm.

The 0.25 ppm. concentration of test compound was obtained as follows: Stock solution C, 20 ml., was diluted with 20 ml. aqueous 0.1 percent polyoxyethylene sorbitan monooleate to give stock solution D. This stock solution D, 4 ml., added to 785 ml. of water in the plastic test containers gave a concentration of test compound of 0.25 ppm.

Three weeks after the date of application of the test compound, measurements were made on the total growth of each plant, as described in Experiment 1, and the percent inhibition observed was calculated using the formula set forth in Experiment 1, above.

The test compound, α-isopropyl-α-(4-trifluoromethoxyphenyl)-3-pyridinemethanol gave an approximate growth inhibition of 97 percent at 1 ppm.; 93 percent at 0.5 ppm; and 93 percent at 0.25 ppm.

I claim:
1. A method for inhibiting the growth of submerged and floating aquatic weeds which comprises adding to the water containing said weeds an amount sufficient to provide a growth inhibiting and non-herbicidal concentration of a compound of the formula

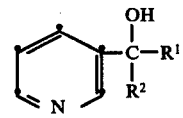

wherein
R¹ is $C_1$–$C_6$ alkyl, phenyl, or $C_3$–$C_8$ cycloalkyl;
R² is trifluoromethoxyphenyl, 1,1,2,2-tetrafluoroethoxyphenyl, pentafluoroethoxyphenyl, or 3,4-(difluoromethylenedioxy)phenyl; and
the nonphytotoxic acid addition salts thereof.

2. The method of claim 1 wherein the active compound is of the formula

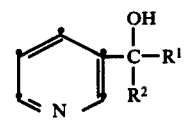

wherein
R¹ is $C_{1-C6}$ alkyl;
R² is trifluoromethoxyphenyl;
and the nonphytotoxic acid addition salts thereof.

3. The method of claim 1 wherein the active compound is a α-isopropyl-α-[p-(trifluoromethoxy)phenyl]-3-pyridinemethanol.

4. The method of claim 1 wherein the growth-inhibiting and non-herbicidal concentration of the active compound ranges from about 0.25 to about 10 ppm.

* * * * *

UNITED STATES PATENT OFFICE
CERTIFICATE OF CORRECTION

Patent No. 4,043,791                     Dated  August 23, 1977

Inventor(s) Eriks V. Krumkalns

It is certified that error appears in the above-identified patent and that said Letters Patent are hereby corrected as shown below:

| | |
|---|---|
| Column 2, line 7: | "3pyridylmethane" should read --3-pyridylmethane--. |
| Column 3, line 15: | "fluoromethylenedioxy)and" should read --fluoromethylenedioxy)phenyl and--. |
| Column 3, line 29: | "3bromopyridine" should read --3-bromopyridine--. |
| Column 4, line 16: | "pyridinemethanol.HCl" should read --pyridinemethanol·HCl--. |
| Column 4, line 19: | "pyridinemethanol.HBr" should read --pyridinemethanol·HBr--. |
| Column 4, line 22: | "cyclohexyl" should read --Cyclohexyl--. |
| Column 5, line 37: | "ph" should read --pH--. |
| Column 6, line 13: | "ph" should read --pH--. |

Signed and Sealed this

Twenty-first Day of February 1978

[SEAL]

Attest:

RUTH C. MASON
*Attesting Officer*

LUTRELLE F. PARKER
*Acting Commissioner of Patents and Trademarks*